United States Patent
Dyballa et al.

(10) Patent No.: US 10,106,497 B2
(45) Date of Patent: Oct. 23, 2018

(54) COUPLING OF TWO ARENES WITH SELENIUM DIOXIDE TO GIVE A SELENOBIARYL ETHER

(71) Applicant: EVONIK DEGUSSA GMBH, Essen (DE)

(72) Inventors: Katrin Marie Dyballa, Recklinghausen (DE); Robert Franke, Marl (DE); Siegfried R Waldvogel, Gau-Algesheim (DE); Thomas Quell, Mainz (DE); Michael Mirion, Mainz (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/157,934

(22) Filed: May 18, 2016

(65) Prior Publication Data

US 2016/0340304 A1  Nov. 24, 2016

(30) Foreign Application Priority Data

May 20, 2015 (EP) .................................... 15168377

(51) Int. Cl.
*C07C 391/02* (2006.01)

(52) U.S. Cl.
CPC .................. *C07C 391/02* (2013.01)

(58) Field of Classification Search
None
See application file for complete search history.

(56) References Cited

U.S. PATENT DOCUMENTS

| | | | |
|---|---|---|---|
| 2015/0336865 A1 | 11/2015 | Dyballa et al. | |
| 2015/0336885 A1 | 11/2015 | Dyballa et al. | |
| 2015/0336995 A1* | 11/2015 | Dyballa ................. | C07F 11/00 568/730 |

FOREIGN PATENT DOCUMENTS

WO    2015/181018 A1    12/2015

OTHER PUBLICATIONS

Waitkins et al. "Selenium Dioxide: Preparation, Properties, and use as Oxidizing Agent", Research Laboratories, Canadian Copper Refiners Limited, Montreal East, Quebec Canada, Feb. 1945, pp. 235-289.*
Engman et al. J. Chem. Soc. Perkin Trans. 2095 (Year: 1988).*
Search Report for European Patent Application No. 15 16 8377 dated Oct. 26, 2015 (2 pages).
Paine et al. Manganese complexes of mixed 0, X, 0-donor ligands (X=S or Se): synthesis, characterization and catalytic reactivity. The Royal Society of Chemistry 2002. 3136-3144.
Paine et al. Polynuclear Nickel(II) Complexes: Preparation and Magnetic Properties of $N^{ii}_4$, $N^{ii}_5$, and $N^{ii}_6$ Species with Ligands containing $O^\frown X^\frown O$ (X=S, Se or N) Donor Atoms. Eur. J. Inorg. Chem. 2003. 3167-3178.
Boyd et al. 470. The Action of Selenious Acid on Alkyl Ethers of Phenols. Journal of the Chemical Society. Jan. 1, 1949. 2196-2197.
Office Action dated Jun. 16, 2017 in Korean Patent Application No. 10-2016-0061263 (14 pages in Korean with English Translation).
Chinese Office Action dated Jul. 7, 2017 relative to Chinese Patent Application No. 201610442462 (11 pages in Chinese with English translation).
Translation of Chinese Search Report for Chinese Office Action dated Jul. 7, 2017 (3 pages).

* cited by examiner

*Primary Examiner* — Clinton A Brooks
(74) *Attorney, Agent, or Firm* — Smith, Gambrell & Russell, LLP

(57) ABSTRACT

The present invention relates to a method for coupling two arenes with selenium dioxide to give a selenobiaryl ether. The method of the present invention includes: adding a first arene to the reaction mixture, adding a second arene to the reaction mixture, adding selenium dioxide to the reaction mixture, adding an acid having a pKa in the range from 0 to 5 to the reaction mixture, and adjusting the reaction temperature of the reaction mixture such that the first arene and the second arene are converted to a selenobiaryl ether. The present invention also relates to novel selenobiaryl ethers.

11 Claims, No Drawings

COUPLING OF TWO ARENES WITH SELENIUM DIOXIDE TO GIVE A SELENOBIARYL ETHER

The invention relates to a method for coupling two arenes with selenium dioxide to give a selenobiaryl ether, and also novel selenobiaryl ethers.

Selenobiaryl ethers are a highly interesting and promising class of compounds. These compounds are currently being incorporated into particular complexes, particularly those containing manganese, but have great potential for further uses.

The term "arenes" is used as a generic term in this application, and therefore also encompasses substituted arenes, but not phenols.

T. K. Paine describes a synthesis of 2,2'-selenobis(4,6-di-tert-butylphenol) using selenium dioxide. The preparation of 2,2'-selenobis(4,6-di-tert-butylphenol) is effected here in an acidic medium with addition of concentrated hydrochloric acid. The product is obtained with a yield of 25% (T. K. Paine et al., "Manganese complexes of mixed O, X, O-donor ligands (X=S or Se): synthesis, characterization and catalytic reactivity", Dalton Trans., 2003, 15, 3136-3144).

It is particularly disadvantageous here that the yields are low and therefore in need of improvement.

It is further problematic that hydrochloric acid is used since this is chlorine-containing. Chlorine-containing species lead to corrosion in steel reactors such that, in industrial scale syntheses, particular measures have to be taken which are frequently linked to major investments (particular reactor materials for example). It is therefore desirable to improve the process.

H. M. Lin describes a synthesis route for selenobiaryl ethers, which is effected over several stages. First of all, bromine has to be added onto the appropriate phenol, in order then to react the product with magnesium to give a Grignard reagent. The Grignard reagent can then react with the added selenium before the actual coupling to give the biaryl ether:

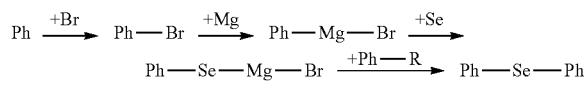

(H. M. Lin et al., "A novel and efficient synthesis of selenides", ARKIVOC, 2012, viii, 146-156)

The product was obtained in a good yield, but this synthesis route is very complex, which makes it unattractive for industrial scale use. In this case, a multitude of synthesis steps are needed, the procedure for which is not uncritical in some cases, especially considering scale-up and using standards which are customary in industry. Moreover, this synthesis route gives rise to large amounts of waste products and solvents which have to be disposed of in a costly and inconvenient manner, one reason for which is the use of bromine.

It was an object of the invention to provide a method which does not have the disadvantages described in connection with the prior art. In particular, a method by which selenobiaryl ethers can be prepared in good yield should be provided. The process should also be usable on the industrial scale, and therefore have a minimum number of individual steps and intermediates.

This object is achieved by a method according to claim 1.

Method for preparing selenobiaryl ethers comprising the method steps of:
a) adding a first arene to the reaction mixture,
b) adding a second arene to the reaction mixture,
c) adding selenium dioxide to the reaction mixture,
d) adding an acid having a pKa in the range from 0 to 5 to the reaction mixture,
e) adjusting the reaction temperature of the reaction mixture such that the first arene and the second arene are converted to a selenobiaryl ether.

Steps a) to d) can be conducted here in any sequence. Accordingly, a reaction mixture is already present in the reaction vessel during the addition or maybe not as in the case of the first addition.

The method is not restricted to the components described above. Further constituents, for example solvents, may likewise be present in the reaction mixture.

If the acid has more than one pKa, the $pKa_1$ should be considered. In the case of the invention, this has to be within the range from 0 to 5. The definition of pKa is sufficiently well known to those skilled in the art and can be found in the appropriate technical literature.

An advantage over the methods described in the prior art is that it is not necessary in this case to work with exclusion of moisture or oxygen. This constitutes a distinct advantage over other synthesis routes. This method stands out advantageously from the existing multistage synthesis routes.

Via the pKa, the reaction can be steered in the direction of selenobiaryl ethers such that the resulting by-products are reduced. As a result of predominant formation of the desired main product and reduction in the formation of higher molecular weight overoxidation products, the workup is distinctly simplified.

Unconverted reactants and solvents used can be recovered by distillation and used for further reactions. Thus, the method according to the invention fulfils the requirements for an economic industrial scale process.

Moreover, selenium dioxide is used in the method according to the invention. Selenium dioxide is a waste product from metal purification and ore refining. Thus, in the method claimed here, a waste product from other processes is reused with addition of value. This is an important topic especially against the background of the sustainability of processes.

In one variant of the method, the first arene in method step a) is a compound of the general formula I:

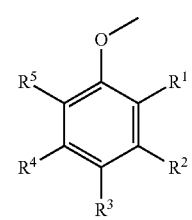

I wherein $R^1$, $R^2$, $R^3$, $R^4$, $R^5$ are each independently selected from:
—H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen (such as Cl, F, Br, I), —OC=O—($C_1$-$C_{12}$)-alkyl,
two adjacent radicals may additionally be joined to one another to form a condensed system,
where the alkyl and aryl groups mentioned may be substituted,
and at least one of the $R^1$, $R^2$, $R^3$, $R^4$, $R^5$ radicals is —H.

($C_1$-$C_{12}$)-Alkyl and O—($C_1$-$C_{12}$)-alkyl may each be unsubstituted or substituted by one or more identical or different radicals selected from:

($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl or alkoxycarbonyl.

($C_6$-$C_{20}$)-Aryl and O—($C_6$-$C_{20}$)-aryl may each be unsubstituted or substituted by one or more identical or different radicals selected from:

—H, —($C_1$-$C_{12}$)-alkyl, —O—($C_1$-$C_{12}$)-alkyl, —O—($C_6$-$C_{20}$)-aryl, -($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

In the context of the invention, the expression ($C_1$-$C_{12}$)-alkyl encompasses straight-chain and branched alkyl groups. Preferably, these groups are unsubstituted straight-chain or branched ($C_1$-$C_8$)-alkyl groups and most preferably ($C_1$-$C_6$)-alkyl groups. Examples of ($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression "—($C_1$-$C_{12}$)-alkyl" also apply to the alkyl groups in —O—($C_1$-$C_{12}$)-alkyl, i.e. in —($C_1$-$C_{12}$)-alkoxy. Preferably, these groups are unsubstituted straight-chain or branched —($C_1$-$C_6$)-alkoxy groups.

Substituted ($C_1$-$C_{12}$)-alkyl groups and substituted ($C_1$-$C_{12}$)-alkoxy groups may have one or more substituents, depending on their chain length. The substituents are preferably each independently selected from:

—($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl or alkoxycarbonyl.

In one variant of the method, $R^1$, $R^2$, $R^3$, $R^4$, $R^5$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, where the alkyl and aryl groups mentioned may be substituted, and at least one of the $R^1$, $R^2$, $R^3$, $R^4$, $R^5$ radicals is —H.

In one variant of the method, $R^1$, $R^2$, $R^3$, $R^4$, $R^5$ are each independently selected from:

—H, —($C_1$-$C_{12}$)-alkyl, —O—($C_1$-$C_{12}$)-alkyl.

where the alkyl and aryl groups mentioned may be substituted, and at least one of the $R^1$, $R^2$, $R^3$, $R^4$, $R^5$ radicals is —H.

In one variant of the method, $R^1$, $R^2$, $R^3$, $R^4$, $R^5$ are each independently selected from:

—H, -CH$_3$, —O—CH$_3$, and at least one of the $R^1$, $R^2$, $R^3$, $R^4$, $R^5$ radicals is —H.

In one variant of the method, the second arene in method step b) is a compound of the general formula II:

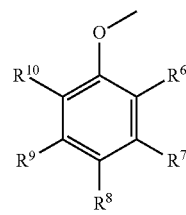

wherein $R^6$, $R^7$, $R^8$, $R^9$, $R^{10}$ are each independently selected from:

—H, —($C_1$-$C_{12}$)-alkyl, —($C_6$-$C_{20}$)-aryl, —O—($C_6$-$C_{20}$)-aryl, -halogen (such as Cl, F, Br, I), —OC═O—($C_1$-$C_{12}$)-alkyl, two adjacent radicals may additionally be joined to one another to form a condensed system, where the alkyl and aryl groups mentioned may be substituted, and at least one of the $R^6$, $R^7$, $R^8$, $R^9$, $R^{10}$ radicals is —H.

In one variant of the method, $R^6$, $R^7$, $R^8$, $R^9$, $R^{10}$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, where the alkyl and aryl groups mentioned may be substituted, and at least one of the $R^6$, $R^7$, $R^8$, $R^9$, $R^{10}$ radicals is —H.

In one variant of the method, $R^6$, $R^7$, $R^8$, $R^9$, $R^{10}$ are each independently selected from:

—H, —($C_1$-$C_{12}$)-alkyl, —O—($C_1$-$C_{12}$)-alkyl, where the alkyl and aryl groups mentioned may be substituted, and at least one of the $R^6$, $R^7$, $R^8$, $R^9$, $R^{10}$ radicals is —H.

In one variant of the method, $R^6$, $R^7$, $R^8$, $R^9$, $R^{10}$ are each independently selected from:

—H, —CH$_3$, —O—CH$_3$, and at least one of the $R^6$, $R^7$, $R^8$, $R^9$, $R^{10}$ radicals is —H.

In one variant of the method, the first arene corresponds to the second arene.

This variant is thus a homo-coupling of two identical arenes which are joined via the selenium.

In one variant of the method, the selenium dioxide is added in method step c) in a molar ratio based on the sum total of the first and second arenes within a range from 0.25 to 1.5.

Preference is given here to the range from 0.25 to 0.9, and particular preference to the range from 0.4 to 0.7.

In one variant of the method, the acid is acetic acid.

In one variant of the method, the acid in method step d) is used as solvent.

In one variant of the method, the reaction mixture is adjusted in method step e) to a temperature in the range from 20° C. to 100° C.

Preference is given here to the range from 50° C. to 100° C., and particular preference to the range from 80° C. to 90° C.

As well as the method, novel selenobiaryl ethers are also claimed.

Compound of the formula 1 or 2:

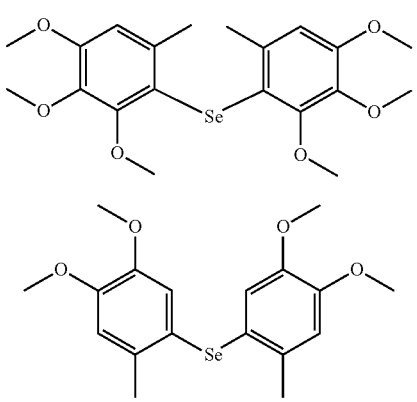

The invention is illustrated in detail hereinafter by working examples.

ANALYSIS

NMR Spectroscopy

The NMR spectroscopy studies were conducted on multinucleus resonance spectrometers of the AC 300 or AV II 400 type from Bruker, Analytische Messtechnik, Karlsruhe. The solvent used was $CDCl_3$. The $^1H$ and $^{13}C$ spectra were calibrated according to the residual content of undeuterated solvent using the NMR Solvent Data Chart from Cambridge Isotopes Laboratories, USA. Some of the $^1H$ and $^{13}C$ signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which need not correspond to IUPAC nomenclature.

Bis(6-methyl-2,3,4-trimethoxyphenyl)selenium

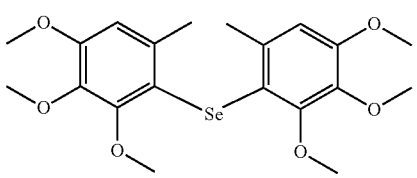

In a 25 mL round-bottom flask, 0.27 g of selenium dioxide (2.4 mmol) was added to 0.80 g of 3,4,5-trimethoxytoluene (4.3 mmol) dissolved in 6 mL of acetic acid and the mixture heated to 85° C. in a hot oil bath. After 12 days, the reaction mixture was filtered, the filtrate diluted with dichloromethane and washed with saturated sodium chloride solution. The organic phase was dried over magnesium sulphate and the solvent distilled off under reduced pressure. The crude product was purified by column chromatography. The column length was 24 cm with a diameter of 3 cm. Cyclohexane/ethyl acetate was used as eluent in a ratio of 9:1.

Yield: 0.399 g (0.9 mmol; 41%)

GC: R (hard method, HP-5)=16.250 min
TLC: $R_f$(CH:EE, 2:1)=0.4 $^1H$-NMR: (400 MHz, CDCl3) δ[ppm]=2.37 (s, 6H), 3.59 (s, 6H), 3.78 (s, 6H), 3.82 (s, 6H), 6.54 (s, 2H).
$^{13}C$-NMR: (100 MHz, CDCl3) δ[ppm]=23.52 56.00, 60.60, 60.86, 109.17, 118.21, 137.07, 140.44, 153.06, 154.19.
HRMS (ESI, pos. mode):m/z for [M+Na+]: calculated: 465.0792 found: 465.0780

Bis(4,5-dimethoxy-2-methylphenyl)selenium

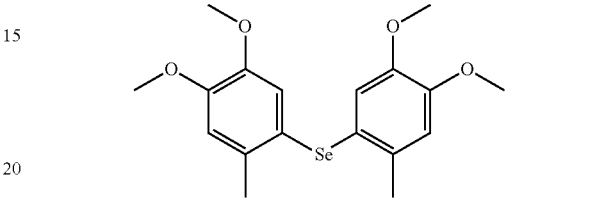

In a 25 mL round-bottom flask, 1.00 g of 3,4-dimethoxytoluene (6.5 mmol) was dissolved in 9 mL of acetic acid, 0.40 g of selenium dioxide (3.6 mmol) was added and the mixture heated to 85° C. in a hot oil bath. After 12 days, the reaction mixture was filtered, the filtrate diluted with dichloromethane and washed with saturated sodium chloride solution. The organic phase was dried over magnesium sulphate and the solvent distilled off under reduced pressure. The crude product was purified by column chromatography. In this case, an automated column system from BÜCHI-Labortechnik GmbH, Essen was used. The column length was 16 cm and the diameter 6 cm. The eluent used was cyclohexane/ethyl acetate, operating with an ethyl acetate gradient of: 0% (over 5 min), 1-5% (over 5 min), 5-10% (over 8 min), 10-20% (8 min), 20-40% (10 min), 40-100% (10 min). The pumping rate was 100 mL/min.

Yield: 0.637 g (1.6 mmol), 51%
GC: R (hard method, HP-5)=15.968 min
$^1H$-NMR: (400 MHz, CDCl3) δ[ppm]=2.34 (s, 6H), 3.70 (s, 6H), 3.86 (s, 6H), 6.76 (s, 2H), 6.77 (s, 2H)
$^{13}C$-NMR: (100 MHz, CDCl3) δ [ppm]=21.96, 56.07, 56.16, 113.47, 116.51, 121.55, 132.50, 147.54, 148.70.
HRMS (ESI, pos. mode):m/z for [M+Na+]: calculated: 405.0581 found: 405.0484

Both compounds 1 and 2 could each be synthesized in very good yields. Therefore, the stated problem is solved by the inventive method.

The invention claimed is:
1. A method for preparing selenobiaryl ethers comprising:
I) forming a reaction mixture by:
  a) adding a first arene to the reaction mixture,
  b) adding a second arene to the reaction mixture,
  c) adding selenium dioxide to the reaction mixture,
  d) adding an acid having a pKa in the range from 0 to 5 to the reaction mixture,
II) adjusting the reaction temperature of the reaction mixture to a temperature in the range from 20° C. to 100° C. such that the first arene and the second arene are converted to the selenobiaryl ether,
wherein the second arene does not include phenols, and wherein the wherein the first arene in method step a) is a compound of the general formula I:

![Formula I structure: methoxybenzene with R1, R2, R3, R4, R5 substituents]

$$\text{I}$$

wherein $R^1$, $R^2$, $R^3$, $R^4$, $R^5$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, two adjacent radicals may additionally be joined to one another to form a condensed system, where the alkyl and aryl groups mentioned may be substituted, and at least one of the $R^1$, $R^2$, $R^3$, $R^4$, $R^5$ radicals is —H.

2. The method according to claim 1, wherein $R^1$, $R^2$, $R^3$, $R^4$, $R^5$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, where the alkyl and aryl groups mentioned may be substituted, and at least one of the $R^1$, $R^2$, $R^3$, $R^4$, $R^5$ radicals is —H.

3. The method according to claim 1, wherein $R^1$, $R^2$, $R^3$, $R^4$, $R^5$, are each independently selected from:

—H, —($C_1$-$C_{12}$)-alkyl, —O—($C_1$-$C_{12}$)-alkyl, where the alkyl groups mentioned may be substituted, and at least one of the $R^1$, $R^2$, $R^3$, $R^4$, $R^5$ radicals is —H.

4. The method according to claim 1, wherein the second arene in method step b) is a compound of the general formula II:

![Formula II structure: methoxybenzene with R6, R7, R8, R9, R10 substituents]

$$\text{II}$$

wherein $R^6$, $R^7$, $R^8$, $R^9$, $R^{10}$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, —OC=O—($C_1$-$C_{12}$)-alkyl, two adjacent radicals may additionally be joined to one another to form a condensed system, where the alkyl and aryl groups mentioned may be substituted, and at least one of the $R^6$, $R^7$, $R^8$, $R^9$, $R^{10}$ radicals is —H.

5. The method according to claim 4, wherein $R^6$, $R^7$, $R^8$, $R^9$, $R^{10}$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, where the alkyl and aryl groups mentioned may be substituted, and at least one of the $R^6$, $R^7$, $R^8$, $R^9$, $R^{10}$ radicals is —H.

6. The method according to claim 4, wherein $R^6$, $R^7$, $R^8$, $R^9$, $R^{10}$ are each independently selected from:

—H, —($C_1$-$C_{12}$)-alkyl, —O—($C_1$-$C_{12}$)-alkyl, where the alkyl and aryl groups mentioned may be substituted, and at least one of the $R^6$, $R^7$, $R^8$, $R^9$, $R^{10}$ radicals is —H.

7. The method according to claim 4, wherein the first arene corresponds to the second arene.

8. The method according to claim 1, wherein the selenium dioxide is added in method step c) in a molar ratio based on the sum total of the first and second arenes within a range from 0.25 to 1.5.

9. The method according to claim 1, wherein the acid is acetic acid.

10. A compound of the formula 1 or 2:

![Compound 1: diaryl selenide structure]

$$1$$

![Compound 2: diaryl selenide structure]

$$2$$

11. The method according to claim 1, wherein the added acid in step d) is present in amounts that forms a solution of dissolved first and second arenes and selenium dioxide.

* * * * *